United States Patent [19]

Rajeckas et al.

[11] 4,454,320

[45] Jun. 12, 1984

[54] PROCESS FOR 5-SUBSTITUTED DIALURIC ACIDS

[75] Inventors: Faustas J. Rajeckas, Waterford; Gerald F. Holland, Old Lyme, both of Conn.

[73] Assignee: Pfizer Inc., New York, N.Y.

[21] Appl. No.: 172,499

[22] Filed: Jul. 28, 1980

[51] Int. Cl.$^3$ ............................................ C07D 239/60
[52] U.S. Cl. ..................................... 544/300; 544/301; 544/302; 544/305
[58] Field of Search ................ 544/300, 302, 305, 301

[56] References Cited

FOREIGN PATENT DOCUMENTS 12882 of 1899 United Kingdom ................ 544/302
1369770 10/1974 United Kingdom ................ 544/302

OTHER PUBLICATIONS

Barton and Ollis, *Comprehensive Organic Chemistry*, pp. 980, 981.
Endo and Okawara, *J. of Organics Chemistry*, V. 45, 2663–2666.
Theilheimer, W.; *Synthetic Methods of Organic Chemistry*, V. 14, No. 711 (1960).
Ashbey, E. C., et al., *J. of Organic Chem.*, 43, pp. 1557 to 1563 (1978).
Theilheimer, W.; *Synthetic Methods of Organic Chemistry*, V. 16, No. 727 (1962).

*Primary Examiner*—Donald G. Daus
*Assistant Examiner*—G. Hendricks
*Attorney, Agent, or Firm*—Charles J. Knuth; Albert E. Frost; Robert K. Blackwood

[57] ABSTRACT

A process for the preparation of certain 5-substituted dialuric acids, compounds having utility as intermediates for the synthesis of certan hypoglycemic 5-substituted oxazolidine-2,4-diones.

22 Claims, No Drawings

PROCESS FOR 5-SUBSTITUTED DIALURIC ACIDS

BACKGROUND OF THE INVENTION

The present invention relates to certain 5-substituted dialuric acids having utility in the synthesis of the corresponding hypoglycemic, 5-substituted oxazolidine-2,4-diones. These hypoglycemic oxazolidine-2,4-diones are the subject of a concurrently filed application, entitled "Hypoglycemic 5-Substituted Oxazolidine-2,4-diones", by Schnur.

Dialuric acids have been previously synthesized by the reaction of alloxan hydrates with aromatic amines, phenols, phenol ethers, pyrrole and certain pyrazolones, e.g.,

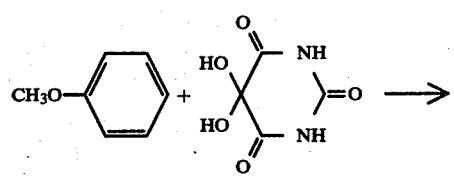

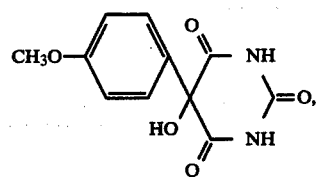

[King and Clark-Lewis, J. Chem. Soc., pp. 3080–3085 (1951)] and by the oxidation of barbituric acids, e.g.,

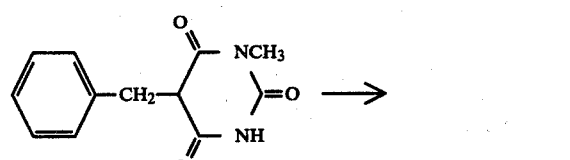

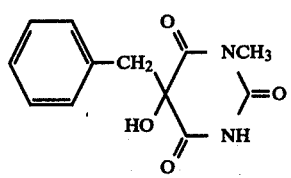

[Aspelund, Acta. Acad. Aboensis, Math. et. Phys. 10 (14), p. 42 (1937); Chem. Abstracts 31; pp. 6632–6633 (1937)]. It is further understood that dialuric acid is the intermediate in the base catalyzed condensation of substituted tartronic esters with urea, e.g.,

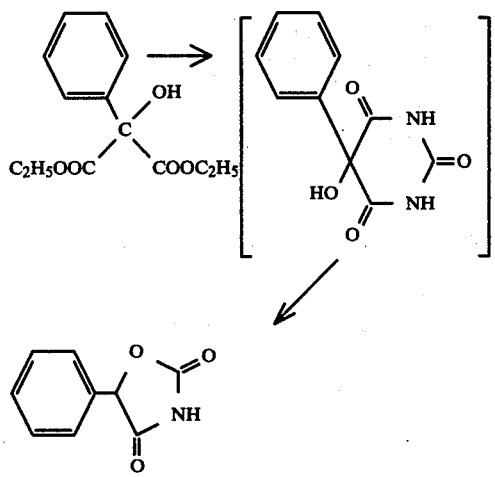

[King and Clark-Lewis, J. Chem. Soc., pp. 3077–3079 (1951)]. The synthesis of oxazolidine-2,4-diones via dialuric acids has been reviewed [Clark-Lewis, Chem. Rev. 58, pp. 68–71 (1958)].

SUMMARY OF THE INVENTION

In spite of its acidic nature, and its content of multiple carbonyl groups, it has been surprisingly found that alloxan (1) reacts with organolithium or Grignard reagents (2) to form 5-substituted dialuric acids [5-hydroxy-2,4,6(1H,3H,5H)pyrimidinetriones, (3)], i.e.,

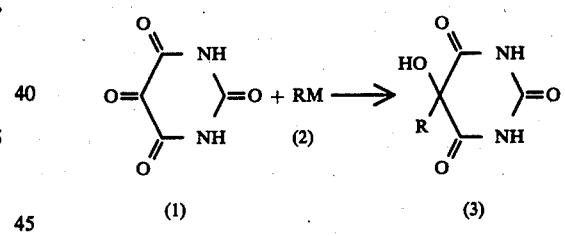

wherein

R represents an organic radical, free of groups, such as carbonyl, carboxylate or hydroxy, which are reactive with the organometal function of RM under the conditions of the reaction (thus causing self-destruction of the reagent); and M represents Li, MgCl, MgBr, MgI, or other suitable organometal functionality. Among these, Li is preferred.

The instant process for dialuric acids, as well as the overall process to the desired oxazolidine-2,4-diones is particularly valuable, in that it is simple to operate, presenting a minimum of potential safety and environmental problems, particularly when requisite starting materials are readily available.

The preferred embodiment of the present invention is a process for the preparation of compounds wherein R is

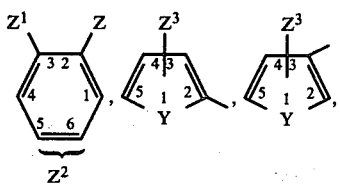

wherein

Z is hydrogen, methyl, ($C_1$-$C_2$)-alkoxy, chloro or fluoro;

$Z^1$ is hydrogen, methyl, chloro or fluoro;

$Z^2$ is hydrogen, methyl, chloro or fluoro (attached to the 5- or 6-position of the phenyl ring);

$Z^3$ is hydrogen, methyl, ($C_1$-$C_2$)-alkoxy, fluoro, chloro, bromo or

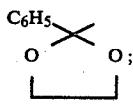

and

Y is sulfur or oxygen;

since the dialuric acids thereby produced have particular value in the preparation of hypoglycemic oxazolidine-2,4-diones.

Particularly valuable in the phenyl series are those compounds wherein $Z^1$ is hydrogen and $Z^2$ is hydrogen, chloro or fluoro. Particularly valuable in the thiophene and furan series are those compounds wherein $Z^3$ is hydrogen, ($C_1$-$C_2$)-alkoxy, chloro or bromo.

The most valuable embodiments of the present invention are the processes for the preparation of dialuric acids wherein R is 3-thienyl, 3-furyl, 2-methoxyphenyl, 2-ethoxyphenyl, 2-methylphenyl, 2-fluorophenyl, 2-methoxy-5-chlorophenyl, and 2-methoxy-5-fluorophenyl, since the 3-thienyl/3-furyl/substituted phenyl halides required for these syntheses are readily available and the ultimately derived oxazolidine-2,4-diones possess exceptional hypoglycemic activity.

DETAILS OF THE INVENTION

It has now been found that alloxan (1) reacts with organometallic salts (2) to yield valuable 5-substituted dialuric acids, which can be converted under mild conditions and in high yield to hypoglycemic 5-substituted oxazolidine-2,4-diones.

The reaction is readily carried out in a reaction-inert solvent, such as those in which the organolithium or Grignard reagents are formed in situ. Representative of such solvents are ether, isopropyl ether, tetrahydrofuran and dioxane. Temperature is not critical, and can be over a broad range (e.g. −90° to 50° C.), provided that the organometallic reagent is of adequate stability at the temperature used. When the stability of the organometallic reagent has not been determined, as a matter of convenience, separate solutions of the reagents are usually combined at low temperature (e.g. −90° to −30° C.) and the action then allowed to proceed to completion at ambient temperature.

The process is broadly applicable to the synthesis of a wide variety of 5-substituted dialuric acids, including, but by no means limited to, those of the formulae

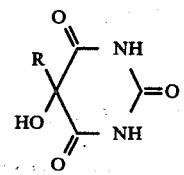

wherein R is

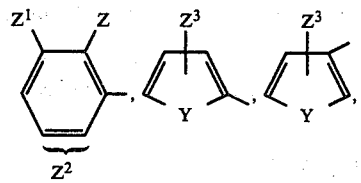

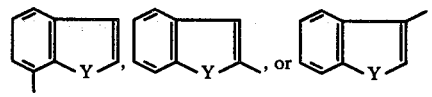

wherein Z, $Z^1$, $Z^2$, $Z^3$ and Y are as defined above.

The requisite organometallic reagents (RM, wherein R and M are as defined above), are generally available in situ from the corresponding halide by known methods. The case wherein M is lithium represents the preferred embodiment of the present invention, particularly when any of Z, $Z^1$, $Z^2$, or $Z^3$ is halogen, since the lithium reagents can be selectively formed, as between chlorine or fluorine and bromine, e.g.,

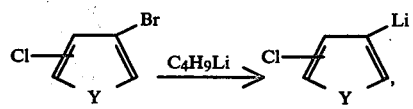

or between bromine at two positions, e.g.

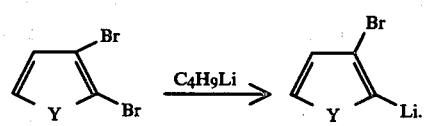

Furthermore, in many instances, the lithium reagent can be formed by exchange, without need for a halide precursor, e.g.,

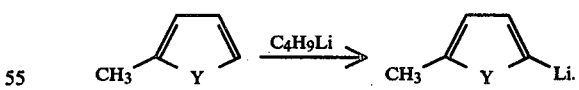

Particularly valuable leading references describing the preparation of organolithium reagents useful in the present invention are Guilard et al., Bull. soc. chim. Fr. (11), pp. 4121–4126 (1967); Zaluski et al., ibid. (5), pp. 1838–1846 (1970); Sornay et al., ibid. (3), pp. 990–1000 (1971); Ly and Schlosser, Helv. Chim. Acta 60 (6), pp. 2085–2088 (1977); MacDowell and Ballas, J. Org. Chem. 42 (23), pp. 3717–3720 (1977); and Chemica Scripta. 15, pp. 1–3 (1980).

Although not essential, it is preferred to use anhydrous alloxan in the present invention. Anhydrous alloxan is readily prepared from alloxan hydrate by sublimation. When alloxan hydrate is used in this invention, at least two equivalents of the organometallic reagent is essential to effect complete conversion, whereas with anhydrous alloxan, only one equivalent of the organometallic reagent is essential for complete conversion.

The halides required for preparation of the organometallic reagents are generally available, commercially or by literature methods. The literature methods cited above will be particularly helpful in connection with furan/thiophene derivatives. The requisite phenyl derivative halides are available commercially, or by standard literature methods such as direct halogenation [e.g., bromination of 4-fluoroanisole to yield 2-bromo-4-fluoroanisole; cf. Weygand, Organic Preparations, Interscience Publishers, New York, 1945, p. 76] or diazotization of amine/halogen replacement [e.g. diazotization of 2-fluoroaniline, followed by reaction with cuprous bromide to yield 2-fluorophenylbromide; cf. Roe in Organic Reactions, Vol. 5, John Wiley and Sons, New York, 1949, p. 193].

The dialuric acids of the present invention are readily converted to the desired hypoglycemic oxazolidine-2,4-diones, e.g., by the action of dilute aqueous sodium hydroxide at ambient temperature for a few minutes. If desired, the dialuric acids need not be isolated, but can be converted in situ, by exposure to mild conditions of aqueous base, directly to oxazolidine-2,4-diones.

The oxazolidine-2,4-diones prepared from the dialuric acids of the present invention are readily adapted to clinical use as antidiabetic agents. The hypoglycemic activity required for this clinical use is defined by the glucose tolerance test procedure which follows. Intact male albino rats are the experimental test animals employed for such purposes. The test animals are fasted approximately 18-24 hours. The rats are weighed, numbered and recorded in groups of five or six as needed. Each group of animals is then dosed intraperitoneally with glucose (one gram per kilogram) and orally with either water (controls) or compound (at a level usually selected from the range 0.1 to 100 mg./kg.). Blood glucose levels (mg./100 ml.) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test.

The oxazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.10 to about 10 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or a pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

The present invention is illustrated by the following examples. However, it should be understood that the invention is not limited to the specific details of these examples.

EXAMPLE 1

5-Hydroxy-5-(5-phenyl-2-furyl)-2,4,6(1H,3H,5H)-pyrimidinetrione

2-Phenylfuran (5.76 g., 40 mmoles) was combined with 100 ml. of tetrahydrofuran and cooled to $-30°$ C. Butyl lithium in hexane (2.3 M, 19.1 ml.) was added dropwise over 5 minutes, keeping the temperature between $-20°$ and $-30°$ C. The reaction mixture was allowed to warm to room temperature and then recooled to $-30°$ C. Sublimed alloxan (5.96 g., 42 mmoles) in 40 ml. of tetrahydrofuran was added over 5 minutes, again keeping the temperature $-20°$ to $-30°$ C. The reaction mixture was again allowed to warm to room temperature, then recooled to $0°$ C. and 50 ml. of 1 N hydrochloric acid added portionwise over 2-3 minutes. The quenched reaction mixture was extracted with 100 ml. of ethyl acetate. The extract was filtered through a bed of anhydrous magnesium sulfate, and evaporated to yield 5-hydroxy-5-(5-phenyl-2-furyl)-2,4,6(1H,3H,5H)pyrimidinetrione [9.4 g., gummy solid, $R_f$ 0.75 (1:1 hexane ethyl acetate/5% acetic acid)] contaminated with starting material ($R_f$ 0.45).

EXAMPLE 2

5-(5-Phenyl-2-furyl)oxazolidine-2,4-dione

5-Hydroxy-5-(5-phenyl-2-furyl)-2,4,6(1H,3H,5H)-pyrimidinetrione (0.7 g.) was dissolved in 15 ml. of 1 N sodium hydroxide, stirred at room temperature for 15 minutes, extracted with ethyl acetate, made slightly acidic with about 1 ml. of glacial acetic acid, and extracted with 25 ml. of ethyl acetate. The latter ethyl acetate extract was back washed with about 6.5 ml. of water, filtered over a bed of anhydrous magnesium sulfate and evaporated to yield solid 5-(5-phenyl-2-furyl)oxazolidine-2,4-dione [100 mg.; m.p. 216°–218° C.; $R_f$ 0.6 (1:1 hexane:ethyl acetate/5% acetic acid)].

EXAMPLE 3

5-Hydroxy-5-(5-methyl-2-furyl)-2,4,6(1H,3H,5H)pyrimidinetrione

2-Methylfuran (3.28 g., 3.58 ml., 40 mmoles) was combined with 100 ml. of tetrahydrofuran. The reaction mixture, flushed with nitrogen, was cooled to −30° C. and butyl lithium (19.1 ml. of 2.3 M in hexane) was added over a period of 10 minutes, maintaining the temperature at −20° to −30° C. The reaction mixture was warmed to room temperature and then back to −30° C. Sublimed alloxan (5.96 g.) in 40 ml. of tetrahydrofuran was added dropwise over 10 minutes, keeping the temperature at −20° to −30° C. The reaction mixture was warmed to room temperature, cooled to 0° C. and 50 ml. of 1 N hydrochloric acid added portionwise, keeping the temperature at 0° to 5° C. The reaction mixture was extracted with 100 ml. of ethyl acetate. The extract was back washed with 25 ml. of water, filtered through a bed of anhydrous magnesium sulfate and evaporated to yield solid 5-hydroxy-5-(5-methyl-2-furyl)-2,4,6-(1H,3H,5H)-pyrimidinetrione (6.3 g.; m/e 224).

EXAMPLE 4

5-(5-Methyl-2-furyl)oxazolidine-2,4-dione

5-Hydroxy-5-(5-methyl-2-furyl)-2,4,6(1H,3H,5H)-pyrimidinetrione (6.3 g.) was dissolved in 50 ml. of 1 N sodium hydroxide and stirred at room temperature for 15 minutes. The reaction mixture was extracted with 50 ml. of ethyl acetate, and acidified with glacial acetic acid. Product was then extracted into fresh ethyl acetate (three 30 ml. portions). The combined ethyl acetate extracts were filtered through a bed of anhydrous magnesium sulfate and evaporated to an oil. The oil was chromatographed on 50 ml. of silica gel, with 1:1 hexane:ethyl acetate/5% acetic acid as eluant. The column was monitored by tlc using the same eluant. Clean product containing fractions were combined, evaporated to dryness and triturated with hexane (311 mg., m.p. 135°–138° C.). Recrystallization from methanol/water afforded purified 5-(5-methyl-2-furyl)oxazolidine-2,4-dione (142 mg., m.p. 136.5°–137.5° C.).

Analysis: Calcd. for $C_8H_7NO_4$: C, 53.04; H, 3.90; N, 7.73. Found: C, 52.82; H, 4.03; N, 7.65.

EXAMPLE 5

5-Hydroxy-5-(3-thienyl)-2,4,6(1H,3H,5H)pyrmidinetrione

Isopropyl ether (40 ml.) was cooled to −70° C. Butyl lithium in hexane (2.4 M, 10 ml., 24 mmoles) was added over 10 minutes, keeping the temperature −70° to −60° C. 3-Bromothiophene (1.9 ml., 20 mmoles) was added over 20 minutes, keeping the temperature −72° to −68° C. The mixture was stirred for an additional 30 minutes at −72° to 70° C. Sublimed alloxan (3 g., 21 mmoles) in 25 ml. of tetrahydrofuran was added over 40 minutes, keeping the temperature −70° to −65° C. Stirring at this temperature was continued for 15 minutes. The cooling bath was removed and the reaction mixture stirred for one hour at room temperature, then cooled to 5° C. Hydrochloric acid (1 N, 40 ml.) was added slowly, and the organic phase separated. The aqueous phase was extracted with 35 ml. of ethyl acetate. The combined organic phase/extract was washed with 10 ml. of water, dried over anhydrous sodium sulfate and concentrated to yield solid 5-hydroxy-5-(3-thienyl)-2,4,6(1H,3H,5H)pyrimidinetrione (1.41 g., 31%; m/e 226).

When this reaction was carried out in tetrahydrofuran with reverse addition of the 3-bromothiophene to butyl lithium, with immediate addition of 0.5 equivalent of alloxan hydrate in place of 1 equivalent of anhydrous alloxan, the product was a mixture of the above trione and 5-(3-bromo-2-thienyl)-5-hydroxy-2,4,6(1H,3H,5H)-pyrimidinetrione, which in turn was converted to a mixture of 5-(3-bromo-2-thienyl)oxazolidine-2,4-dione and 5-(3-thienyl)oxazolidine-2,4-dione by the method of Example 6.

Alternatively 3-bromothiophene in isopropyl ether is reacted with magnesium turnings to form the corresoponding Grignard reagent. Anhydrous alloxan in tetrahydrofuran is added dropwise and 5-hydroxy-5-(3-thienyl)-2,4,6(1H,3H,5H)-pyrimidinetrione isolated as above. As a further alternative, either 3-iodothiophene or 3-chlorothiophene is used as the substrate for formation of a Grignard reagent, then reacted with alloxan.

EXAMPLE 6

5-(3-Thienyl)oxazolidine-2,4-dione

5-Hydroxy-5-(3-thienyl)-2,4,6(1H,3H,5H)pyrimidinetrione (1.16 g., 5.1 mmoles) was dissolved in 1 N sodium hydroxide (11 ml., 11 mmoles) and allowed to stand at room temperature for 15 minutes. The solution was acidified with acetic acid, and product allowed to crystallize over 35 minutes. Filtration gave 5-(3-thienyl)oxazolidine-2,4-dione (480 mg., 51%; m.p. 133°–135° C.). An additional crop of product was obtained by extracting the mother liquor with ethyl acetate. The extract was back washed with water, and evaporated to dryness (80 mg., contaminated with starting material).

EXAMPLE 7

5-(3-Furyl)-5-hydroxy-2,4,6(1H,3H,5H)pyrimidinetrione

The detailed procedure of Example 5, but substituting 3-bromofuran (2.94 g., 1.8 ml., 20 mmoles) for the 3-bromothiophene, was employed to produce 5-(3-furyl)-5-hydroxy-2,4,6(1H,3H,5H)pyrimidinetrione (1.62 g., oil, m/e 210).

EXAMPLE 8

5-(3-Furyl)oxazolidine-2,4-dione 5-(3-Furyl)-5-hydroxy-2,4,6(1H,3H,5H)pyrimidinetrione (1.62 g.) was dissolved in 15 ml. of 1 N sodium hydroxide, and allowed to stand for 15 minutes at room temperature, and then extracted with 5 ml. of ethyl acetate. The aqueous layer was acidified with glacial acetic acid (about 1.5 ml.) and product extracted into 25 ml. of ethyl acetate. The extract was back washed with 5 ml. of water, filtered through a bed of anhydrous sodium sulfate, and evaporated to yield crude product as an oil (470 mg., m/e 167). Crystallization from chloroform gave purified 5-(3-furyl)oxazolidine-2,4-dione (129 mg., m.p. 88°–90° C., m/e 167). A second, lower melting crop was obtained from mother liquor.

EXAMPLE 9

5-Hydroxy-5-(5-methoxy-2-thienyl)-2,4,6(1H,3H,5H)-pyrimidinetrione

2-Methoxythiophene (2.3 g., 20 mmoles) was dissolved in 35 ml. of ether. With cooling, butyl lithium in hexane (2.4 M, 9ml., 21.6 mmoles) was added dropwise over 15 minutes, the temperature rising as high as 35° C. during this addition. The reaction mixture was stirred for 1 hour at room temperature. While maintaining the temperature between −20° and −15° C., sublimed alloxan (3 g., 21 mmoles) in 20 ml. of tetrahydrofuran was added during 10 minutes. The mixture was warmed to room temperature, stirred for 0.5 hour, cooled to 5° C. and quenched by adding 35 ml. of 1 N hydrochloric acid in portions. The organic phase was separated and the aqueous phase extracted with 25 ml. of ethyl acetate. The combined organic phase and extract were back-washed with water, concentrated to dryness and triturated with hexane to yield solid 5-hydroxy-5-(5-methoxy-2-thienyl)-2,4,6(1H,3H,5H)-pyrimidinetrione (1.4 g., m/e 256).

EXAMPLE 10

5-(5-Methoxy-2-thienyl)oxazolidine-2,4-dione

5-Hydroxy-5-(5-methoxy-2-thienyl)-2,4,6(1H,3H,5H)-pyrimidinetrione (1.1 g.) was dissolved in 10 ml. of 1 N sodium hydroxide, allowed to stand for 1.5 hours at room temperature, extracted with ether, acidified with acetic acid, diluted with 15 ml. of water and filtered to yield product [567 mg., m.p. 144°–146° C. (dec.)]. Recrystallization from acetone-hexane gave purified 5-(5-methoxy-2-thienyl)oxazolidine-2,4-dione in two crops [487 mg., m.p. 147°–148° C. (dec.)].

Analysis: Calcd. for $C_8H_7O_4NS$: C, 45.08; H, 3.31; N, 6.57. Found: C, 45.08; H, 3.41; N, 6.39.

EXAMPLE 11

5-[5-(2-phenyl-1,3-dioxolan-2-yl)-2-thienyl]-2,4,6(1H,3H,5H)-pyrimidinetrione At room temperature, 2-phenyl-2-thienyl-1,3-dioxolane (3.26 g., 14 mmoles) was dissolved in 35 ml. of ether. Butyl lithium in hexane (2.4 M, 6.25 ml., 15 mmoles) was added dropwise over 15 minutes, the temperature rising to 33° C. The mixture was stirred for 75 minutes at room temperature and then cooled. Maintaining the temperature between −15° and −20° C., sublimed alloxan (2.13 g., 15 mmoles) in 20 ml. of tetrahydrofuran was added dropwise over 10 minutes. The reaction mixture was stirred at room temperature for 30 minutes, cooled to 5° C., quenched with 35 ml. of 1 N hydrochloric acid, added in small portions, and extracted with 25 ml. of ethyl acetate. The organic layer was back washed with 15 ml. of water, filtered through a bed of anhydrous sodium sulfate, and evaporated to yield 5-[5-(2-phenyl-1,3-dioxolan-2-yl)thienyl]-2,4,6(1H,3H,5H)-pyrimidinetrione [oil, $R_f$ 0.25 (1:1 hexane:ethyl acetate/5% acetic acid)] contaminated with starting material ($R_f$ 0.8).

EXAMPLE 12

5-[5-(2-Phenyl-1,3-dioxolan-2-yl)-2-thienyl]oxazolidine-2,4-dione

The entire crude product from the preceding Example was taken into 35 ml. of 1 N sodium hydroxide and allowed to stand for 30 minutes. After acidification the product was extracted into isopropyl ether. The extract was back washed with water and evaporated to yield 5-[5-(2-phenyl-1,3-dioxolan-2-yl)thienyl]-oxazolidine-2,4-dione [0.40 g., $R_f$ 0.65 (1:1 ethyl acetate:hexane/5% acetic acid)].

EXAMPLE 13

5-(5-Benzoyl-2-thienyl)oxazolidine-2,4-dione

5-[5-(2-Phenyl-1,3-dioxolan-2-yl)-2-thienyl]-oxazolidine-2,4-dione (0.04 g.) was dissolved in 30 ml. of ether and stirred with 10 ml. of 6 N hydrochloric acid at room temperature for 1 hour. Ethyl acetate (10 ml.) was added, and the organic layer was separated and evaporated in vacuo to dryness (0.388 g.). Chromatography on 50 ml. of silica gel, eluted with 1:1 hexane:ethyl acetate/5% acetic acid and monitored by tlc, gave in early fractions purified 5-(5-benzoyl-2-thienyl)oxazolidine-2,4-dione (0.22 g., m.p. 153°–155° C., m/e 287).

Analysis: Calcd. for $C_{14}H_9O_4NS$: C, 58.52; H, 3.16; N, 4.87. Found: C, 58.69; H, 3.50; N, 4.94.

EXAMPLE 14

5-(4-Bromo-2-furyl)-2,4,6(1H,3H,5H)pyrimidinetrione n-Butyl lithium is reacted with 2,4-dibromofuran in ether according to the procedure of Sornay et al. [Bull. soc. chim. Fr., p. 998 (1971)]. The resulting organolithium solution is reacted with alloxan at −60° to −65° C. according to Example 5, affording 5-(4-bromo-2-furyl)-2,4,6(1H,3H,5H)pyrimidinetrione.

EXAMPLE 15

5-(4-Bromo-2-furyl)oxazolidine-2,4-dione

The procedure of Example 2 is employed to convert 5-(4-bromo-2-furyl)-2,4,6(1H,3H,5H)pyrimidinetrione to 5-(4-bromo-2-furyl)oxazolidine-2,4-dione.

EXAMPLE 16

5-(3-Chloro-2-furyl)-2,4,6(1H,3H,5H)pyrimidintrione n-Butyl lithium and an equivalent of diisopropylamine are reacted with an equivalent of 3-chlorofuran for 1.5 hours in tetrahydrofuran at −80° C. according to the procedure of Ly and Schlosser [Helv. Chim. Acta 60 (6), p. 2087 (1977)]. At the same temperature, an equivalent of alloxan in tetrahydrofuran is added dropwise and the mixture allowed to warm to room temperature for 2 hours. 5-(3-Chloro-2-furyl)-2,4,6-(1H,3H,5H)pyrimidinetrione is isolated by the procedure of Example 5.

EXAMPLE 17

5-(3-Chloro-2-furyl)oxazolidine-2,4-dione

The procedure of Example 2 is employed to convert 5-(3-chloro-2-furyl)-2,4,6(1H,3H,5H)pyrimidinetrione to 5-(3-chloro-2-furyl)oxazolidine-2,4-dione.

EXAMPLE 18

5-(3-Bromo-2-furyl)-2,4,6(1H,3H,5H)pyrimidinetrione n-Butyl lithium is reacted with 2,3-dibromofuran in ether at −70° C. according to the procedure of Zaluski et al. [Bull. soc. chim. Fr., p. 1843 (1970)] and Sornay et al. [loc. cit., p. 990 (1971)]. The reaction mixture is warmed to −20° C. and an equivalent of anhydrous alloxan in tetrahydrofuran is added dropwise. Reaction is allowed to proceed to completion by warming to room temperature for 2 hours. The product, 5-(3- bromo-2-furyl)-2,4,6(1H,3H,5H)pyrimidinetrione is isolated according to the method of Example 5.

The required organolithium is alternatively prepared from 3-bromofuran as a tetrahydrofuran solution at −80° C. by the method of Ly and Schlosser [Helv. Chim. Acta. 60 (6), p. 2087 (1977)]. In this case, the alloxan is added at −80° C. (cf. Example 16).

EXAMPLE 19

5-(3-Bromo-2-furyl)oxazolidine-2,4-dione

The procedure of Example 2 is employed to convert 5-(3-bromo-2-furyl)-2,4,6(1H,3H,5H)pyrididinetrione to 5-(3-bromo-2-furyl)oxazolidine-2,4-dione.

EXAMPLE 20

5-(2-Chloro-3-thienyl)-2,4,6(1H,3H,5H)pyrimidinetrione

Following the method of Gronowitz et al. [Chemica Scripta 15, p. 2 (1980)], 2-chloro-3-bromothiophene is reacted with n-butyl lithium in ether at −70° C. After 15 minutes, the organolithium reagent is poured into a solution of alloxan in tetrahydrofuran at −70° C. The reaction mixture is allowed to warm to room temperature for 2 hours, and 5-(2-chloro-3-thienyl)-2,4,6(1H,3H,5H)-pyrimidinetrione isolated according to Example 5.

The same procedure is employed with 4-bromo-2-chlorothiophene to produce 5-(5-chloro-3-thienyl)-2,4,6(1H,3H,5H)pyrimidinetrione.

EXAMPLE 21

5-(2-Chloro-3-thienyl)oxazolidine-2,4-dione

The procedure of Example 2 is employed to convert 5-(2-chloro-3-thienyl)-2,4,6(1H,3H,5H)pyrimidinetrione to 5-(2-chloro-3-thienyl)oxazolidine-2,4-dione.

The same procedure is employed to convert 5-(5-chloro-3-thienyl)-2,4,6(1H,3H,5H)pyrimidinetrione to 5-(5-chloro-3-thienyl)oxazolidine-2,4-dione.

EXAMPLE 22

5-Hydroxy-5-(2-methoxy-3-furyl)-2,4,6(1H,3H,5H)pyrimidinetrione

2-Methoxy-3-bromothiophene is reacted with n-butyl lithium in ether at 0° to 5° C., following the method of Sornay et al. [Bull. soc. chim. Fr. (3), p. 999 (1971)]. The organolithium reagent is cooled to −10° to −20° C. and reacted with an equivalent of alloxan in tetrahydrofuran. The reaction mixture is allowed to warm to room temperature and 5-hydroxy-5-(2-methoxy-3-furyl)-2,4,6(1H,3H,5H)pyrimidinetrione isolated according to the method of Example 5.

EXAMPLE 23

5-(2-Methoxy-3-furyl)oxazolidine-2,4-dione

The procedure of Example 2 is employed to convert 5-(2-methoxy-3-furyl)-2,4,6(1H,3H,5H)-pyrimidinetrione to 5-(2-methoxy-3-furyl)oxazolidine-2,4-dione.

EXAMPLE 24

5-(3-Fluoro-2-furyl)-5-hydroxy-2,4,6(1H,3H,5H)pyrimidinetrione

By the procedure of Example 16, 3-fluorofuran is converted to 5-(3-fluoro-2-furyl)-5-hydroxy-2,4,6-(1H,3H,5H)pyrimidinetrione.

EXAMPLE 25

5-(3-Fluoro-2-furyl)oxazolidine-2,4-dione

The procedure of Example 2 is employed to convert 5-(3-fluoro-2-furyl)-5-hydroxy-2,4,6(1H,3H,5H)pyrimidinetrione to 5-(3-fluoro-2-furyl)oxazolidine-2,4-dione.

EXAMPLE 26

5-(3-Benzo[b]furyl)-5-hydroxy-2,4,6(1H,3H,5H)pyrimidinetrione

3-Bromobenzo[b]furan [Mason et al., J. Chem. Soc., p. 3150 (1931)] is reacted with n-butyl lithium and then with alloxan, following the procedure of Example 5, to yield 5-(3-benzo[b]furyl)-5-hydroxy-2,4,6(1H,3H,5H)pyrimidinetrione.

Alternatively, 3-bromobenzo[b]furan in isopropyl ether is reacted with magnesium turnings at room temperature in the presence of a catalytic amount of methyl iodide to form the Grignard reagent. Sublimed alloxan in tetrahydrofuran is added dropwise and product isolated according to Example 5.

EXAMPLE 27

5-(3-Benzo[b]furyl)oxazolidine-2,4-dione

The procedure of Example 2 is employed to convert 5-(3-benzo[b]furyl)-5-hydroxy-2,4,6(1H,3H,5H)pyrimidinetrione to 5(3-benzo[b]furyl)oxazolidine-2,4-dione.

EXAMPLE 28

5-Phenyl (and Substituted Phenyl)-5-hydroxy-2,4,6(1H,3H,5H)pyrimidinetriones

By the procedure of Example 5, phenyl bromide, 2-bromoanisole, 2-ethoxyphenyl bromide, 2-bromo-4-fluoroanisole, 2-bromo-4-chloroanisole, 2-bromotoluene and 2-fluorophenyl bromide are converted, respectively, to:
5-hydroxy-5-phenyl-2,4,6(1H,3H,5H)pyrimidinetrione,
5-hydroxy-5-(2-methoxyphenyl)-2,4,6(1H,3H,5H)pyrimidintrione;
5-(2-ethoxyphenyl)-5-hydroxy-2,4,6(1H,3H,5H)pyrimidintrione;
5-(5-fluoro-2-methoxyphenyl)-5-hydroxy-2,4,6(1H,3H,5H)pyrimidintrione;
5-(5-chloro-2-methoxyphenyl)-5-hydroxy-2,4,6(1H,3H,5H)pyrimidintrione;
5-hydroxy-5-(2-methylphenyl)-2,4,6(1H,3H,5H)pyrimidintrione, and
5-(2-fluorophenyl)-5-hydroxy-2,4,6(1H,3H,5H)pyrimidintrione.

Alternatively, 2-chloroanisole, 2-bromoanisole or 2-iodoanisole is converted to the corresponding Grignard reagent by reaction with magnesium turnings in diisopropyl ether. The reagent is chilled and reacted with anhydrous alloxan according to Example 5 to yield 5-(hydroxy-5-(2-methoxyphenyl)-2,4,6(1H,3H,5H)pyrimidintrione.

EXAMPLE 29

5-Phenyl (and Substituted Phenyl) oxazolidine-2,4-diones

By the procedure of Example 2, the various pyrimidintriones of Example 28 are converted to:
5-phenyloxazolidine-2,4-dione;
5-(2-methoxyphenyl)oxazolidine-2,4-dione;

5-(2-ethoxyphenyl)oxazolidine-2,4-dione;
5-(5-fluoro-2-methoxyphenyl)oxazolidine-2,4-dione;
5-(5-chloro-2-methoxyphenyl)oxazolidine-2,4-dione;
5-(2-methylphenyl)oxazolidine-2,4-dione; and
5-(2-fluorophenyl)oxazolidine-2,4-dione.

PREPARATION 1

2-Phenyl-2-(2-thienyl)-1,3-dioxolane

2-Benzoylthiophene (19 g., 0.1 mole), ethylene glycol (11 ml., 0.2 mole), toluene (150 ml.) and p-toluenesulfonic acid (about 0.2 g.) were combined and refluxed for 6 hours. By-product water was collected in a Dean-Stark trap. Tlc (1:8 ethyl acetate:hexane) indicated reaction to be about 40% complete. More ethylene glycol (30 ml.) was added and reflux continued for 35 hours. Reaction was still incomplete. The reaction mixture was diluted with 200 ml. of ether, washed twice with 150 ml. portions of water and concentrated to dryness. The residue was chromatographed on about 500 ml. of silica gel, with 1:8 ethyl acetate:hexane as eluant, monitored by tlc. Faster moving, product containing fractions were combined and evaporated to yield 2-phenyl-2-(2-thienyl)-1,3-dioxolane [8 g., oil, $R_f$ 0.6 (1:8 ethyl acetate:hexane)].

We claim:

1. A process for preparing a compound of the formula

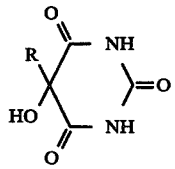

which comprises the step of reacting anhydrous alloxan with substantially one equivalent of an organometallic reagent of the formula

RM in a reaction inert solvent at a temperature of −90° to 50° C., in which formulae R is an organic radical free of groups which will cause self-destruction of the organometallic reagent at the particular temperature of the reaction and M is Li or MgX, wherein X is Cl, Br or I.

2. A process of claim 1 wherein R is

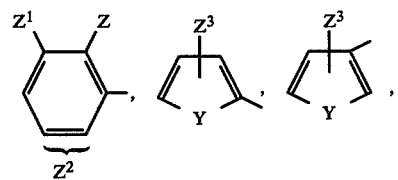

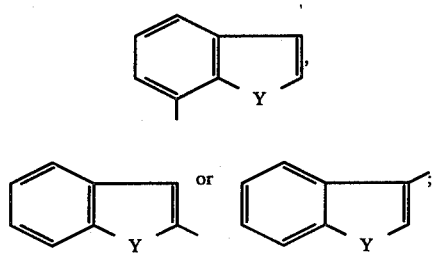

Z is hydrogen, methyl, $(C_1-C_2)$-alkoxy, chloro or fluoro;

$Z^1$ is hydrogen, methyl, chloro or fluoro;

$Z^2$ is hydrogen, methyl, chloro or fluoro;

$Z^3$ is hydrogen, methyl, phenyl, $(C_1-C_2)$-alkoxy, fluoro, chloro, bromo or

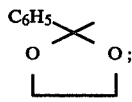

and

Y is sulfur or oxygen.

3. A process of claim 2 wherein M is Li.

4. A process of claim 3 wherein R is

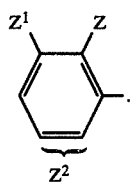

5. A process of claim 4 wherein $Z^1$ is hydrogen and $Z^2$ is hydrogen, chloro, or fluoro.

6. The process of claim 5 wherein Z is methoxy and $Z^2$ is hydrogen.

7. The process of claim 5 wherein Z is ethoxy and $Z^2$ is hydrogen.

8. The process of claim 5 wherein Z is fluoro and $Z^2$ is hydrogen.

9. The process of claim 5 wherein R is

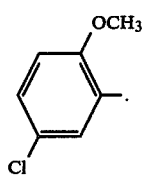

10. The process of claim 5 wherein R is

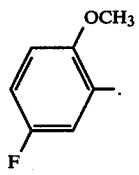

11. A process of claim 3 wherein R is

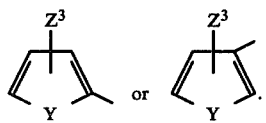

12. A process of claim 11 wherein R is

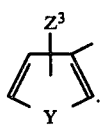

13. A process of claim 12 wherein $Z^3$ is hydrogen.
14. The process of claim 13 wherein Y is sulfur.
15. The process of claim 13 wherein Y is oxygen.
16. A process of claim 3 wherein R is

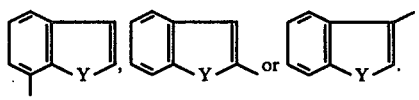

17. A process of claim 16 wherein Y is oxygen.

18. A process of claim 17 wherein R is

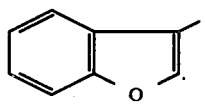

19. A process of claim 2 wherein M is MgCl, MgBr or MgI.
20. A process of claim 19 wherein R is

21. A process of claim 20 wherein Y is sulfur.
22. The process of claim 21 wherein M is MgBr.

* * * * *